(12) United States Patent
Nassal et al.

(10) Patent No.: US 8,282,932 B2
(45) Date of Patent: Oct. 9, 2012

(54) SPLIT-CORE-PARTICLES FOR THE PRESENTATION OF FOREIGN MOLECULES, ESPECIALLY FOR VACCINE APPLICATIONS, AND METHOD FOR THEIR PRODUCTION

(75) Inventors: Michael Nassal, March (DE); Claudia Skamel, Freiburg (DE); Andreas Walker, Freiburg (DE)

(73) Assignee: Universitatsklinikum Freiburg, Freiburg (DE)

( * ) Notice: Subject to any disclaimer, the term of this patent is extended or adjusted under 35 U.S.C. 154(b) by 399 days.

(21) Appl. No.: 12/440,454

(22) PCT Filed: Jul. 12, 2007

(86) PCT No.: PCT/EP2007/006190
§ 371 (c)(1),
(2), (4) Date: May 5, 2009

(87) PCT Pub. No.: WO2008/028535
PCT Pub. Date: Mar. 13, 2008

(65) Prior Publication Data
US 2010/0040646 A1   Feb. 18, 2010

(30) Foreign Application Priority Data
Sep. 8, 2006   (EP) ..................................... 06018847

(51) Int. Cl.
*A61K 39/29*   (2006.01)
*A61K 39/00*   (2006.01)

(52) U.S. Cl. ................ 424/189.1; 424/184.1; 424/185.1; 435/69.1; 536/23.1

(58) Field of Classification Search ......................... None
See application file for complete search history.

(56) References Cited

U.S. PATENT DOCUMENTS
2003/0175863 A1   9/2003   Birkett

OTHER PUBLICATIONS

Nassal et al. (Eur. J. Immunology published Jan. 24, 2005, vol. 35, p. 655-665).*
Lu et al. (Intervirology, 2001, vol. 44, p. 124-131).*
Tetteh, "Progress and Challenges towards the Development of Malaria Vaccines" Biodrugs, 2007, 21(6):357-373.*
Vogel, et al., "Quaternary Structure is Critical for Protein Display on Capsid-Like Particles (CLPs): Efficient Generation of Hepatitis B Virus CLPs Presenting Monomeric but not Dimeric and Tetrameric Fluorescent Proteins", Proteins Structure Function and Bioinformatics, vol. 58 (2), pp. 478-488 (Feb. 2005).
Vogel, et al., "In Vitro Assembly of Mosaic Hepatitis B Virus Capsid-Like Particles (CLPs): Rescue into CLPs of Assembly-Deficient Core Protein Fusions and FRET-Suited CLPs", FEBS Letters, Elsevier, Amsterdam, NL, vol. 579 (23), pp. 5211-5216 (Sep. 2005).
Skamel, Claudia et al., "Hepatitis B Virus Capsid-Like Particles Can Display the Complete, Dimeric Outer Surface Protein C and Stimulate Production of Protective Antibody Responses Agaist *Borrelia burgdorferi* Infection", Journal of Biological Chemistry, vol. 281 (25), pp. 17474-17481 (Jun. 2006).
O'Shea, E K et al., "Peptide 'Velcro*': Design of a Heterodimeric Coiled Coil", Current Biology, Current Science, vol. 3 (10) pp. 658-667 (1993).
Walker, Andreas et al., "SplitCore: An Exceptionaly Versatile Viral Nanoparticle for Native Whole Protein Display Regardless of 3D Structure", Scientific Reports. Jun. 2011; 1(5) Supplement: 1-8.
Whitacre, David C. et al., "Use of Hepadnavirus Core Proteins as Vaccine Platforms", *Expert Rev Vaccines*. Nov. 2009; 8(11): 1565-1573.

* cited by examiner

*Primary Examiner* — Bo Peng
(74) *Attorney, Agent, or Firm* — Chalin A. Smith; Smith Patent Consulting

(57) ABSTRACT

Disclosed are split-core carrier substance which, as separate polypeptide, have the core N domain and the core C domain of the core protein of a hepatitis B virus and at least one foreign molecule against which an immune response is to be induced. According to the invention, the foreign molecule, especially the heterologous foreign amino acid sequence, is fused to the C terminus or the core N domain or to the N terminus of the core C domain and the core protein can form capsid-like particles. The invention also relates to the associated production method.

22 Claims, 9 Drawing Sheets

Figure 1:
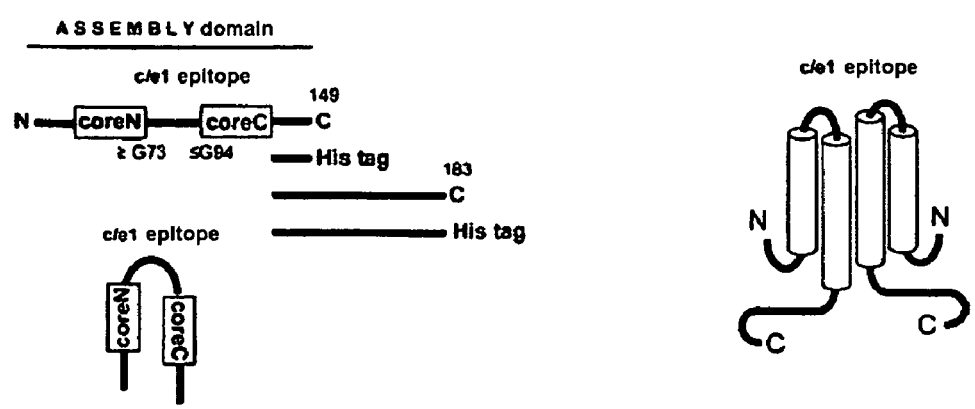

Fig. 1: Diagrammatic representation of the core protein structure

Figure 2:
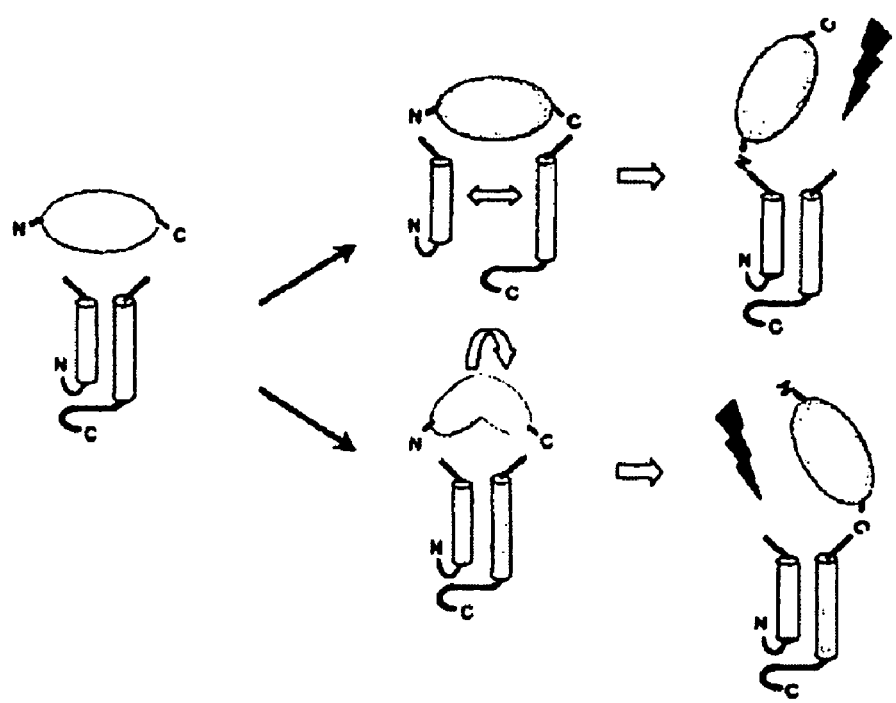

Fig. 2: Principle of the split-core system

Figure 3:
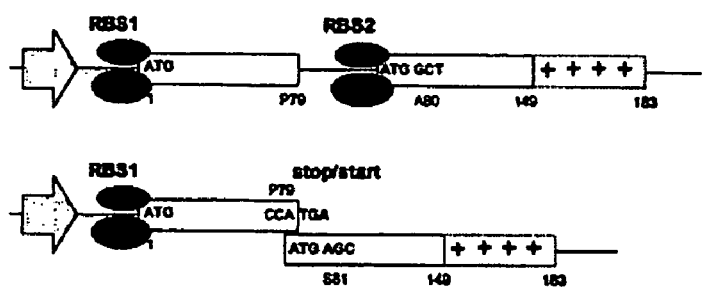

Fig. 3 Diagrammatic representation of two implementations of bacterial expression vectors for approximately equimolar production of the two coreN and coreC fragments

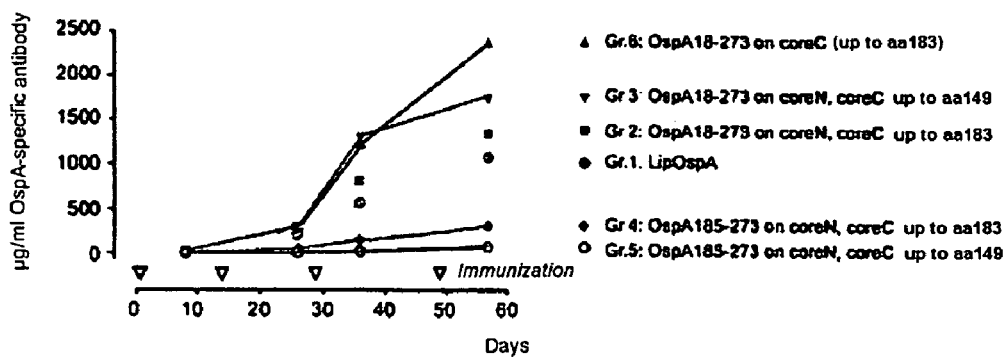
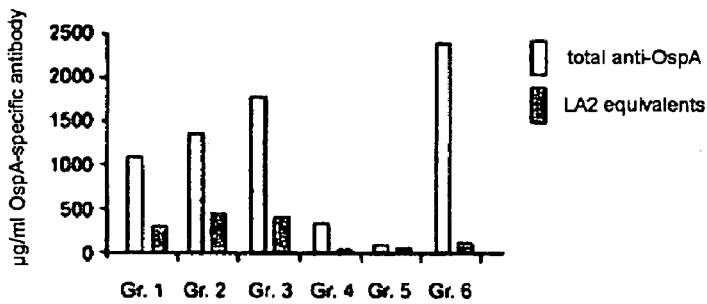
Figure 4

Fig. 5: Principle of region-specific directed induction of antibodies to a foreign protein in the split-core system

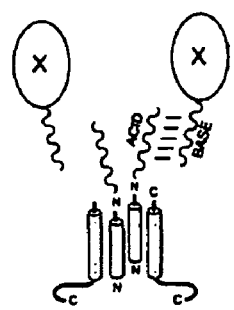
Fig. 6: Split-core fusion with interaction-capable, flexibly exposed foreign molecule

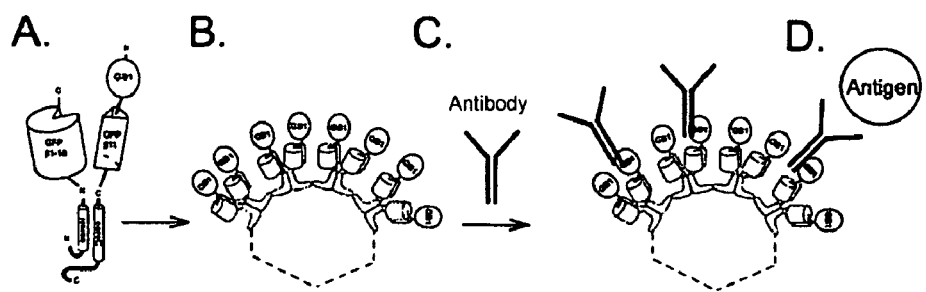
Fig. 7: Principle of self-fluorescent split-core CLPs presenting an interaction-capable foreign molecule, here GB1, on their surface

| | Arthritis, Day 52 | | protected from infection |
|---|---|---|---|
| Mouse group, passively immunized with | Marked | Weak | |
| | | | |
| LA-2, 5 µg | 1/6 | 1/6 | 4/6 |
| LA-2, 1 µg | 2/6 | 3/6 | 1/6 |
| | | | |
| LipOspA, 5 µg | 0/6 | 1/6 | 5/6 |
| LipOspA, 1 µg | 1/6 | 0/6 | 5/6 |
| | | | |
| Split-coreOspA on coreN, 5 µg of LA-2-equivalent antibodies | 0/6 | 0/6 | 6/6 |
| Split-core OspA on coreN, 1 µg of LA-2-equivalent antibodies | 0/6 | 0/6 | 6/6 |
| | | | |
| Split-core OspA on coreC, vol. equivalent to 5 µg of LA-2-eq., with OspA on coreN | 2/6 | 0/6 | 4/6 |
| Split-core OspA on coreC, vol. equivalent to 1 µg of LA-2 eq. with OspA on coreN | 3/6 | 2/6 | 1/6 |
| | | | |
| Mouse normal serum | 3/3 | 0/3 | 0/3 |

Figure 8: Protective potential of different anti-OspA immune sera against challenge of SCID mice with B. burgdorferi

| Immunogen | Week (pb = post-boost) | Rec. CSP | NANP | NVDP | Rec. HBc | CSP12 peptide | CSP8 peptide |
|---|---|---|---|---|---|---|---|
| HBc149 CSP repeat cont. | wk 8 | Not determined | $1.25 \times 10^5$ | $5 \times 10^3$ | $6.25 \times 10^5$ | Not determined | Not determined |
| | wk 6 pb | $3 \times 10^6$ | $3 \times 10^6$ | $6.25 \times 10^5$ | $3 \times 10^6$ | 0 | 0 |
| Split-core149-CSP short | wk8 | Not determined | $1.25 \times 10^5$ | $5.0 \times 10^3$ | $1.25 \times 10^5$ | Not determined | Not determined |
| | wk6 pb | $3 \times 10^6$ | $3 \times 10^6$ | $6.25 \times 10^5$ | $1.25 \times 10^5$ | $2.5 \times 10^4$ | 0 |
| Split-core149-CSP full-length | wk8 | Not determined | $1.25 \times 10^5$ | $2.5 \times 10^4$ | $2.5 \times 10^4$ | Not determined | Not determined |
| | wk6 pb | $12 \times 10^6$ | $3 \times 10^6$ | $6.25 \times 10^5$ | $1.25 \times 10^5$ | $2 \times 10^2$ | $2.5 \times 10^4$ |

Figure 9: B cell responses to CSP and core carrier after single immunization or two immunizations of B10 mice with the immunogens indicated

SPLIT-CORE-PARTICLES FOR THE PRESENTATION OF FOREIGN MOLECULES, ESPECIALLY FOR VACCINE APPLICATIONS, AND METHOD FOR THEIR PRODUCTION

This application corresponds to the national phase of International Application No. PCT/EP07/006,190, filed Jul. 12, 2007, which, in turn, claims priority to European Patent Application No. 06.018847.1 filed Sep. 8, 2006, both of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on May 7, 2012, is named LNK-048 Final Sequence Listing.txt and is 9,088 bytes in size.

This application corresponds to the national phase of International Application No. PCT/EP07/006,190, filed Jul. 12, 2007, which, in turn, claims priority to European Patent Application No. 06.018847.1 filed Sep. 8, 2006, both of which are incorporated by reference herein in their entirety.

The present invention relates to novel carriers for vaccines but also for other molecules, based on the hepatitis B virus core antigen. Foreign amino acid sequences which may be from pathogens are incorporated into the hepatitis virus core antigen. The vaccine is intended to enable antibodies to these protein sequences to be produced, with preference being given to protective or neutralizing antibodies. The particles of the invention may also stimulate the cellular immune response (T cells). The hepatitis B core protein has the property of multiple copies being able to form capsid-like particles. These capsid-like particles (CLPs) are particularly suited to the production of vaccines because they stimulate the immune system and thereby increase antibody production. The expression "vaccine" preferably means in the present application a carrier system which may elicit both humoral and cellular immune responses.

Capsids of hepatitis B viruses are nanoparticles of icosahedral symmetry (diameter: approx. 30 nm) which consist of 180 or 240 copies of the viral core protein. The core protein is called HBcAg. They may serve as particulate carriers for foreign molecules and are preferably applied as immuno enhancing antigen carriers for vaccines. Suitable modification of the core protein enables the foreign molecules to be presented on the particle surface (also inside, if required). Surface exposition is optimized by linking the foreign molecule to aa residues in the center of the aa sequence of the core protein (aa region of approx. 73-94) which include the immunodominant B-cell epitope "c/e1" and which have the highest exposition on the particle surface in the 3D structure (aa means amino acid).

WO 01/77158 describes hepatitis B core antigen fusion proteins, where heterologous epitopes are inserted preferably in the region between positions 61 and 90. US 2003/0198649 describes hepatitis B virus core antigen particles in which the immunogens are connected via ligand structures to the hepatitis B virus (HBV) core protein. Kratz et al. [PNAS (1999), 1915-1920] describe GFP (green fluorescent protein) presentation on the surface of the HBV core protein. Here, amino acids 79 and 80 of the core protein were replaced with the 238 amino acid GFP sequence.

Nassal et al. [Eur. J. Immunol. (2005), pp. 655-665] describe a fusion product of the entire *Borrelia burgdorferi* OspA protein and the hepatitis B virus capsid protein. Here too, amino acids 79 and 80 were replaced, with amino acids 18 to 273 of OspA, but with linker sequences being incorporated between core protein and OspA. Skamel et al. (Journal of Biological Chemistry, 2006. pages 17474-17481) describe presentation of the complete OspC protein of *Borrelia burgdorferi* with the aid of hepatitis B virus capsid-like particles. However, the modified core proteins of the solutions disclosed in the prior art have been found having no longer a tendency toward forming capsid-like particles (CLPs) in the desired manner and therefore no longer stimulate the immune response satisfactorily.

This means that, when genetically inserting foreign molecules based on peptides or proteins into the core protein, the foreign sequence is connected both via its N terminus and via its C terminus to the core protein. The linkage on both sides has now been found to drastically eliminate the type and selection of suitable foreign sequences.

The split-core system described herein removes these limitations by generating the core protein in two separate parts which surprisingly come together spontaneously and form capsid particles in a manner similar to the continuous protein chain. Foreign molecules may be fused either to the N-terminal fragment ("coreN") or to the C-terminal fragment ("coreC") and are therefore linked to the carrier protein only via one end. As a result, the structural limitations of the linkage on both sides with regard to the insertion of foreign sequences into the continuous peptide chain of the core protein are essentially removed.

The split-core system of the invention therefore permits:
(i) the presentation of foreign molecules which, due to their size and/or structure, can be presented in the conventional continuous core protein context only very poorly or not at all;
(ii) the presentation of heterodimeric foreign proteins;
(iii) the presentation of interactive foreign molecules in a flexible, well accessible form which substantially facilitates interaction with the desired partner molecules;
(iv) the presentation of additional foreign molecules via the additional surface-exposed N and C termini which are present in the split-core system but not in the conventional continuous core system.

Hepatitis B viruses (HBVs) are enveloped viruses. The inner nucleocapsid is also referred to as core particle ("core") and is defined serologically as hepatitis B core antigen (HBcAg). Cores consist of 180 or 240 copies of the 183-185 aa core protein (depending on the HBV subtype). The core protein may be expressed heterologously (in bacteria, yeast, eukaryotic cells), with "capsid-like particles" (=CLPs) being formed spontaneously. The latter are not infectious since they contain neither the viral genome nor the outer envelope. Such CLPs can also be obtained from the more closely related mammalian HBVs (for example woodchuck; grounds squirrel; and others) and the more distantly related avian HBVs (for example duck; heron; and others). It is possible according to the invention to employ in principle any HBV sequences but preference is being given to the sequences of HBVs capable of infecting humans.

The amino acid sequence and nucleotide sequence of the HBV core protein have been disclosed [Galibert et al., Nature (1979), pp. 646-650; Nassal, Gene (1988), pages 279-294 or WO 01/77158], and reference is made to these publications. Preference is given to employing the core protein sequence of the ayw subtype (e.g., SEQ ID NO: 16) but it is also possible to use likewise variants, modifications of the HBV sequence such as the sequence of other mammalian HBVs or avian HBVs. The sequences are stored in the publicly accessible gene libraries.

Apart from the human pathogenic hepatitis B virus (HBV in the narrow sense) there are a number of related, animal-specific hepatitis B viruses, for example the North American woodchuck (zoological name Marmota monax; woodchuck hepatitis B virus=WHV) HBV (woodchuck hepatitis B virus=WHV), the Californian ground squirrel (zoological name: *Spermophilus beecheyi*) HBV (ground squirrel hepatitis B virus=GSHV), and others.

These viruses possess a genetic structure similar to that of human HBV but have distinct differences in their nucleotide sequence and thus amino acid sequence of their proteins.

The use of human HBV core as vaccine carrier is subject to two possible limitations:

1. Subjects suffering from a chronic HBV infection are partially tolerant to HBV antigens (this lack of immune response is jointly responsible for the infection's persistence). Core also acts as a T-cell-dependent antigen. T-cell epitopes in the core protein sequence are therefore involved in the strong immunogenicity of vaccines based on HBV core CLPs. This would possibly have no effect in individuals chronically infected with HBV, due to their T-cell tolerance to HBV core. However, there is no such tolerance to core of WHV and other animal HBVs (cf. Billaud J N. et al. *Advantages to the use of rodent hepadnavirus core proteins as vaccine platforms*. Vaccine. 2007 Feb. 19; 25(9): 1593-606). Using an animal HBV core protein as carrier might therefore be advantageous to this special circle of potential subjects to be vaccinated.

2. Owing to its extraordinary strong immunogenicity, core elicits a strong anti-core B-cell response (anti-HBcAg) in all subjects acutely or chronically infected with HBV; cured infections are additionally characterized by the appearance of antibodies to the HBV envelope proteins (anti-HBsAg). Current prophylactic vaccines to HBV infection are based exclusively on the HBV envelope protein (HBsAg). A successful vaccination therefore causes the appearance of anti-HBsAg, just like an infection that has been overcome. Whether a subject has acquired anti-HBsAg via infection or via HBsAg vaccination, is of diagnostic interest in some cases and can be decided by the detection of anti-HBcAg which occurs only after infection.

A vaccine based on human HBV core would also elicit a certain anti-core (anti-HBcAg) response in addition to the desired response to the inserted foreign protein. With anti-HBsAg being present at the same time, this would make the distinction between HBV infection and HBsAg vaccination more difficult.

Production of anti-HBcAg has been minimized in the split-core system, since the major epitope, namely c/e1, has been physically separated and can therefore no longer be recognized by the majority of anti-HBcAg antibodies. A residual anti-HBcAg response to other sequence regions of the core protein is present, however. This response can be prevented or further reduced by using a non-human HBV core protein, preferably the WHV core protein, as carrier base.

The essential components of the split-core carrier system of the invention are firstly the core protein of a hepatitis B virus and secondly the foreign molecule to which an immune response is to be elicited.

The core protein in its broadest embodiment is derived from any hepatitis B virus. Various hepatitis B viruses are known. Preference is given to employing according to the invention those sequences which are derived from hepatitis B viruses that have been isolated from mammals and are specific to these. Particular preference is given to employing human HBV. In addition to this, however, it is also possible for those hepatitis B viruses providing the sequence of the core protein to originate from other animals, for example birds such as ducks or herons.

The other component, namely the foreign molecule to which an immune response is to be elicited, may be in principle any molecule. Preference is given here to protein sequences and particularly preferably to those protein sequences which are found on the surfaces of pathogens and which make contact with the immune system. If the immune system is able to produce antibodies to such surface structures of pathogens, the latter are inactivated after contact with the individual components of the immune system of the vaccinated patient, with the pathogenic invader normally being destroyed.

A comparison of the woodchuck hepatitis B virus (WHV) sequences available in databases with the amino acid of the core protein of HBV (ayw subtype, SEQ ID NO: 16) finds an identity of about 60%. Differences in the sequences are particularly prominent in the region between amino acid positions 66 and 94, and this sequence includes the c/e1 epitope and, in the HBV split-core system of the invention, the dividing site between the N-terminal region and the C-terminal region of the core protein. In a particularly preferred embodiment, this dividing site is between amino acids 79 and 81.

WHV split-core carrier systems of the invention were prepared by separating the WHV core protein sequence at the nucleic acid level between position 79 (codes for the amino acid Glu) and position 80 (codes for the amino acid glutamine). At the nucleotide level, a sequence encoding BamH1 cleavage site was added to the carboxy terminus of the N-terminal core protein segment of WHV (abbreviated as WcoreN). Downstream thereof followed a second ribosomal binding site and an Nde1 restriction endonuclease cleavage site which in turn overlaps with the start codon of the WHV coreC (WcoreC) segment. This arrangement is identical with the preferred arrangement in the corresponding HBV split-core constructs. This enables insertions to be transferred directly from one system to the other one with the aid of a BamH1-Nde1 digestion. In the case described here, WcoreN contains a conservative substitution, namely E79D, and additionally a P as C-terminal amino acid, due to the introduced BamH1 cleavage site. This has no adverse effect on the ability to form particles, and the C-terminal proline, owing to its protease resistance, increases the stability of the split protein. Like HBV split core, WcoreC contains an additional start methionine, in this case upstream of Q80 (S81 in HBV). This WHV split-core construct formed particles equally as well as the corresponding HBV split-core construct.

In a further embodiment of the present invention, the C-terminal region and the N-terminal region of the core protein may originate from different hepatitis B viruses. In this case, the hybrid split-core carrier system of the invention has essentially three components, the N-terminal core protein region from a hepatitis B virus, for example a human hepatitis B virus, the foreign molecule to which an immune response may be elicited and the C-terminal region of the core protein which originates from another hepatitis B virus, for example from WHV. Such a hybrid split-core construct also formed particles without any problems. Since the amino acid sequences of the core proteins from different hepatitis B viruses are different, the B- and T-cell epitopes also differ. The hybrid split-core system can therefore specifically influence the immune response to the particulate carrier.

Preferred hybrid split-core carrier systems of the invention were prepared by separating the WHV core protein sequence at the nucleic acid level between position 79 (codes for the amino acid Glu) and position (codes for the amino acid glutamine). At the nucleotide level, a sequence encoding BamH1 cleavage site was added to the carboxy terminus of the N-terminal core protein segment of WHV (abbreviated as WcoreN). Downstream thereof followed a second ribosomal binding site and an Nde1 restriction endonuclease cleavage site which in turn overlaps with the start codon of the WHV coreC (WcoreC) segment. This arrangement is identical with the preferred arrangement in the corresponding HBV split-core constructs. This enables insertions to be transferred directly from one system to the other one with the aid of a BamH1-Nde1 digestion. In the case described here, WcoreN contains a conservative substitution, namely E79D, and additionally a P as C-terminal amino acid, due to the introduced BamH1 cleavage site. This has no adverse effect on the ability to form particles, and the C-terminal proline, owing to its protease resistance, increases the stability of the split protein. Like HBV split core, WcoreC contains an additional start methionine, in this case upstream of Q80 (S81 in HBV). This construct was able to form particles without problems.

Natural HBcAg as well as recombinant HBV CLPs are highly immunogenic (T cell-independent and T cell-dependent antigen). The symmetric, multimeric particulate structure of the core particle is essential here. Said structure can be depicted by conventional negative stain electromicroscopy and also be cryo electron microscopy. The particulate nature can be detected biochemically by sedimentation in sucrose gradients (sedimentation coefficient of 60-80 S, depending on the variant; for comparison: soluble monomeric proteins: approx. 1-5 S; eukaryotic ribosomal subunits: 40S+60S). In addition, the particles have a distinct migration behavior in native gel electrophoresis in agarose gels, which is different from that of nonparticulate forms. This makes it possible to determine whether CLPs can form or whether the proteins are present without CLP structure.

The HBV core protein has 183 or 185 amino acids (the WHV protein has 187 amino acids) and consists of two domains: the first approx. 140 aa are required and sufficient for CLP assembly (assembly domain); the C-terminal region is rich in basic aa and binds nucleic acids. A C-terminally truncated core protein variant (aa1-149) was expressed in the original *E. coli* expression systems substantially better than the full length protein. CLPs of core protein 1-149, i.e. without nucleic acid binding domain, were therefore utilized for medium and high resolution EM structural studies. Thus it was possible to determine the crystal structure of the CLPs and of the protein. As has been predicted biochemically, the core protein forms very stable, symmetrical dimers which assemble to give CLPs comprising 90 or 120 dimers.

BRIEF DESCRIPTION OF THE DRAWINGS

FIG. 1 depicts diagrammatically the core protein structure.

FIG. 2 depicts the principle of the split-core system.

FIG. 3 depicts the preferred expression vectors.

FIG. 4A depicts the kinetics of induction of total anti-OspA antibodies.

FIG. 4B depicts the comparison of anti-OspA Ab titers.

FIG. 5 depicts the principle of region-specific directed induction of antibodies to a foreign protein in the split-core system.

FIG. 6 depicts split-core fusion with interaction-capable, flexibly exposed foreign molecule.

FIG. 7 depicts the principle of self-fluorescent split-core CLPs presenting an interaction-capable foreign molecule, here GB1, on their surface.

FIG. 8 depicts protective potential of different anti-OspA immune sera against challenge of SCID mice with *B. burgdorferi.*

FIG. 9 depicts B cell responses to CSP and core carrier after single immunization or two immunizations of B10 mice with the immunogens indicated.

The core particles have conspicuous spikes; each dimer forms a spike whose structure consists of a bundle of 4 helices, with each monomer contributing two long a-helices in the center of the aa sequence. The spike tips comprise the amino acids (aa) in the aa 74-85 region. This region also carries the immunodominant B-cell epitope of HBcAg (c/e1 epitope), and its particularly high immunogenicity can be explained by the surface exposition of these residues.

FIG. 1 depicts diagrammatically the core protein structure. The primary sequence of the HBV core protein is depicted on the left-hand side of FIG. 1. The entire protein consists of 183 aa (185 aa in some HBV subtypes); only the N-terminal approx. 140 aa are required for CLP formation (assembly domain); a preferred C-terminal aa position is 149; a His tag may be fused to this position and to any downstream aa, up to aa183, without disturbing the CLPs. The c/e1 epitope is located in the region of aa78-83 and forms part of the loop between the central α-helices (bottom left). The helices themselves may be truncated, with probably the aa residues up to position Gly73 in core N and the residues from aa Gly94 onward in coreC being the required minimum. The right-hand side of FIG. 1 depicts a diagrammatic representation of a core protein dimer. Only the two center helices per monomer are shown. The c/e1 epitope is located on the particle surface.

For a successful particle formation, the core aa sequence must include at least position 140, preferably at least position 149, but may also extend further up to the C-terminal aa183 or 185, depending on the HBV subtype. The aa sequence downstream of position 140, better 149, may be replaced with foreign sequences which are then usually located inside the CLPs. Antibodies are not primarily produced against such foreign amino acids they may fulfill other functions, however.

Owing to the extraordinarily high immunogenicity of HBcAg, recombinant HBV CLPs are attractive for use as immunogenicity-enhancing carrier for foreign antigens.

An alternative solution is chemical coupling of foreign molecules to preformed CLPs. The present invention provides a genetic fusion of foreign aa sequences to the core protein. The region of the c/e1 epitope proved here to be best suited to inducing potent B-cell responses, on the basis of empirical trials and even before the X-ray crystallography structure had been resolved. It has now become clear, on the basis of said structure, that such fusions represent insertions into the loop between the center helices. Since this loop does not have per se any structural function, the 3D structure of the core protein may, at least in principle, be retained upon insertion of foreign sequences. Depending on the foreign sequence inserted, some of those fusion proteins may continue to form regular CLPs although this is not always guaranteed because the foreign amino acid sequence may adversely affect forming of the fusion protein structure. The particulate structure for its part is essential for high immunogenicity.

A multiplicity of foreign sequences has previously been inserted into the core protein, and in some cases increased immunogenicity has also been detected experimentally [Ulrich et al., Adv. Virus Res. (1998), pp. 141-182]. However, since many attempts of inserting relatively long foreign sequences, with more than approx. 40 aa, failed (particles no longer being formed), it was assumed that there is a naturally limited capacity for receiving foreign sequences of up to 40 aa or, in a special case, up to 120 aa.

Foreign amino acid sequences fused at the C terminus and the N terminus to the core protein were found to form particles only, if at least two essential criteria are met:

(i) the 3D structure of the foreign protein must be such that its N terminus and C terminus fit in with the spatial position of the linkage points in the core protein (C terminus of the N-terminal core moiety, i.e. core aa from approx. 1 to approx. 78 [coreN]; N terminus of the C-terminal core moiety, i.e. core aa from approx. 80 to 149 or 183 [coreC]);
(ii) if the foreign protein itself makes homomeric interactions (dimers, trimers, etc.), the structure of these homo-oligomers must likewise fit in with the structure of the two core protein moieties.

Foreign proteins whose N and C termini are in close proximity in the native 3D structure are therefore well suited to presentation in previously disclosed fusion proteins. GFP meets both of these requirements but many other proteins do not; one example of the latter is the outer surface protein A (OspA) of the Lyme disease pathogen, *Borrelia burgdorferi*, whose N and C termini are on opposite sides of the long 3D structure.

Insertion of OspA or other proteins with a similarly unfavorable structure results in tensions in the fusion protein. Either, the foreign protein remains correctly folded and prevents the two core protein moieties from approaching each other, thus preventing their folding and subsequent dimerization and particle formation; or, folding of the core protein moiety impairs folding of the foreign protein which either is no longer native (>altered antigenicity) or—if massively misfolded—leads to aggregation.

In the case of OspA, this problem was circumvented only partially by utilizing very long linker sequences. These linker sequences represent a potential problem, especially for vaccine applications, in that they could have undesired antigenicity of their own, possibly resulting in harmful cross reactions, for example with endogenous antigens. Moreover, corresponding protein preparations had only very limited capability of forming regular CLPs.

In addition, general steric hindrance could be a problem with very large foreign proteins or foreign proteins which greatly deviate from a globular structure, owing to the dimeric structure of the core protein carrier and the geometrically limited surface of the carrier particles (the space available on the "spherical surface" of the CLPs is limited). The maximum size of the foreign protein depends on several factors. The method of the invention has already succeeded in presenting a foreign protein of approx. 320 aa (CSP).

The present invention therefore relates to a split-core vaccine which has as separate polypeptides, the core N domain and the core C domain of the core protein of a hepatitis B virus and at least one foreign amino acid sequence to which a humoral and, where appropriate, a cellular immune response is to be elicited, said foreign amino acid sequence being fused to the C terminus of the core N domain or to the N terminus of the core C domain and the core protein being able to bind capsid-like particles. Preference is given to the carrier system eliciting neutralizing antibodies.

It is essential for the core protein in the split-core vaccine of the invention to be interrupted, that is separated, at the c/e1 epitope, i.e. approximately between amino acids 73 and 94. The foreign amino acid sequence may then be fused to the C-terminal end of the core N region. In this case, the N-terminal end of the core C part starts with the amino acid at which the core N protein was separated. It is also possible that part of the c/e1 epitope is deleted, i.e. that one or more amino acids have been removed from the region between amino acids 73 and 94. Alternatively, it is possible for the foreign amino acid sequence to which antibodies are to be produced to be fused to the N-terminal end of the core C region. In this case, the C-terminal region of core N terminates at the amino acid at which the core protein has been interrupted. A substantial effect which must be retained by the split-core vaccine is that of the split-core vaccine particles carrying foreign amino acid sequences fused thereto still being able to form the core capsid-like particles. This is tested either in a sucrose gradient or in native agarose gel electrophoresis. A test with the aid of an electron microscope is also possible.

The foreign amino acid sequence to which antibodies are to be produced is preferably a sequence originating from surface structures of microorganisms. Such microorganisms usually cause diseases in humans. If neutralizing antibodies to these structures can be produced, then this results in the immune defense being able to remove very rapidly invading microorganisms. A bacterium for which vaccine development is already quite advanced is *Borrelia burgdorferi*, the Lyme disease pathogen. Foreign amino acid sequences which are preferably employed within the scope of the invention are the *Borrelia burgdorferi* surface proteins OspA and OspC. However, the foreign amino acid sequences may also be other sequences originating from pathogenic organisms. An example of these is the malaria pathogen, *Plasmodium falciparum*.

Other foreign amino acid sequences to which antibodies can be produced are sequences originating from viruses. Preference is given to employing those amino acid sequences which originate from proteins of viruses coming into contact with the immune system of the host organism. Said proteins are primarily surface proteins, since these are usually the first ones contacting the immune system of the host organism. Alternatively, however, there may also be proteins which are released in the course of the viral lifecycle. Depending on the type of virus, they may be viral core proteins or nucleocapsid proteins, for example.

However, the present split-core vaccine may be used for generating not only antibodies to exogenous amino acid sequences but also antibodies to undesired endogenous structures such as tumor markers, for example. Tumor cells frequently express other surface markers than healthy cells. Thus, if such endogenous amino acid sequences are presented in the split-core vaccine, an immune response is elicited, causing the body to increasingly produce antibodies to said tumor cells. These antibodies enable the immune defense to readily recognize and ultimately eliminate the tumor cells. However, the carrier system of the invention may also induce the cellular immune response which may improve efficiency.

The present application also relates to a method of preparing a vaccine against a heterologous protein sequence. The split-core vaccine consists of two parts of the core antigen of a hepatitis B virus, with either the heterologous protein sequence being fused to the core N region or the core C protein being fused to the C-terminal end of the heterologous protein sequence. The position in the amino acid chain, at which the two domains are separated from another, is located between position 73 and position 94. Individual amino acids of this amino acid region which represent the c/e1 epitope may be deleted.

The method of the invention may be carried out in principle in two different ways. If the two parts of the split-core antigen are expressed as only a single polypeptide chain, a recognition sequence for a protease is inserted according to the invention at the desired position. This enables the expressed polypeptide to be cleaved into two defined parts by the protease. It is also possible in this embodiment for the protease which cleaves at the desired cleavage site to be coexpressed. The gene sequence coding therefor may be located either on the same vector or on a separate vector.

In another, preferred embodiment, the two polypeptides mentioned above are expressed using a special vector, however. Preference is given to employing a "bicistronic" vector. This means that one part of the split-core vaccine is expressed as polypeptide chain and that a stop codon is located at the C terminus. Shortly thereafter, however, the ribosomes can attach again and express the second polypeptide. This ensures that both parts of the split-core vaccine are produced in about equal amounts and there is no need for taking care that the host organism does not lose either of the vectors, which would result in only one part of the split-core vaccine still being provided.

The expression "fusion protein" or "fused to" means that two different proteins or polypeptides are connected with one another via a peptide bond. Such fusion proteins are produced by expressing the nucleic acid sequences coding therefor, which are connected in series.

Linking the inserted foreign protein on both sides, via its N and C termini, was found in the present invention to be the main protein-chemical problem with regard to a broader usability of the HBV-CLP carrier system (specifically as vaccine carrier, generally for presentation of foreign molecules). The number and type of insertable foreign proteins increases drastically, if either of the two covalent bonds (on the N- or C-terminal side of the insert) can be dissolved and particles form nevertheless because the separated core protein moieties (split core) find each other and fold correctly. This is an essential aspect of the present invention.

FIG. 2 depicts diagrammatically that insertion of a foreign protein with an unfavorable 3D structure (e.g. OspA) may prevent formation of the particle formation-competent structure of the core protein carrier (upper path); alternatively, formation of the correct 3D structure of the core protein carrier may prevent formation of the native 3D structure of the foreign protein (bottom path). This would adversely affect the binding of the desired antibodies. This steric problem is eliminated, if either of the two covalent linkages between foreign protein insert and carrier (on the C-terminal or the N-terminal side of the insert) is dissolved (arrow). One way of achieving this is subsequent cleavage of a continuous fusion protein, which requires a cleavage site for a specific protease to be introduced additionally. Preference is therefore given to expressing the two fragments as separate entities from the outset.

The solution according to the invention has still further consequences:

(i) since the c/e1 epitope is located on the particle surface, the new N and C termini form on this surface, which can be derivatized further. For example, a foreign molecule X can be fused to the coreN fragment and a foreign molecule Y can be fused to the coreC fragment. A possible application is the presentation of heterodimeric foreign molecules. It must be taken into account here, however, that there must not be any steric hindrance of the two parts attached by fusion.

(ii) specific subregions of an inserted foreign sequence, for example a particularly important epitope, may be oriented toward the particle surface or away from it, depending on the linkage via N terminus or C terminus. One example is the "LA2 epitope" of B. burgdorferi OspA, which has been found to be located in the C-terminal region. Antibodies which recognize this epitope have neutralizing action.

This is also important for inserting foreign sequences which on their part present further interaction surfaces (see examples for the attachment of third molecules). Since the interaction-capable foreign sequence is linked only on one side, no artificial 3D structure is forced upon it; rather, depending on the type, it is flexible or can form its correct 3D structure without interference. This substantially facilitates interactions with the interaction partner.

The present invention also relates to medicaments, in particular vaccines, which comprise capsid-like particles based on the split-core system.

The medicaments of the invention include the capsid-like particles of the invention, and they preferably influence the immune system positively. Usually, the split-core carrier system of the invention presents to the immune system a foreign amino acid sequence to which the immune system produces antibodies, preferably neutralizing antibodies. These antibodies are then decisively involved in controlling the microorganism that has invaded the body or the virus, or they assist the specific destruction of undesired tumor cells.

In a further embodiment, the split-core carrier system of the invention may be employed as a diagnostic and/or analytical means. Examples 12 and 13 illustrate such applications in more detail. With such means it is possible, for example, to make accessible self-fluorescent, antibody-binding particles which for their part bind antigen and make it visible by way of fluorescence. In a further embodiment, the split-core carrier systems of the invention may comprise peptide sequences which bind specifically determined metal ions/lanthanides. If such peptides are incorporated into the split-core system, particles are provided which comprise multiple reporter atoms/ions of this kind per individual particle and are better detectable.

EXAMPLE 1

Wild-Type Core Protein with Inserted TEV-Protease Recognition Sequence

A recognition sequence for tobacco etch virus (TEV) protease was introduced into the c/e1 epitope of wt core protein 1-149 (substitution of aa P79+A80 by GGGGT-ENLYFQGT-GGGG (SEQ ID NO: 1); G residues as linkers to ensure accessibility of the recognition sequence to the protease). The recombinantly expressed protein formed particles. These were incubated with TEV protease and the success of the cleavage reaction was checked by means of SDS PAGE. The protease digestion mixture was then sedimented through a sucrose gradient. Virtually complete cleavage occurred at the expected position, since two fragments of nearly equal size were produced. Despite cleavage, the protein sedimented in the gradient to about the same position as uncleaned wt core protein 1-149. Comparable results were obtained using a fusion protein based on the full-length core protein 1-183.

EXAMPLE 2

Core Protein Variants with Relatively Large Inserted Foreign Sequences

As an example of a fusion protein with moderately large insertion, the sequence for an artificial peptide, "ACID" (SEQ ID NO: 19) (flanked by Gly-rich linkers; 65 aa in total) which can interact with a complementary peptide, "BASE" (SEQ ID NO: 20). In the complementary BASE peptide which forms heterodimers with ACID, the amino acid residues e (=Glu) are replaced by K (=Lys). Herein, the sequence for the artificial "ACID" peptide, (SEQ ID NO: 19), was inserted into the c/e1 epitope [O'Shea et al., Curr. Biol. (1993), 656-667]; the TEV-protease recognition sequence GGGGSGGG-VEDGGGGSGGGT-AQLEKELQALE- KENAQLEWELQALEKELAQTG-ENLYFQGTGGGG (SEQ ID NO: 2) was inserted in the downstream thereof.

The fusion protein formed CLPs. These were isolated and incubated as above with TEV protease. Here too specific cleavage occurred but the particles remained intact. In this case, the TEV cleavage fragments have different sizes and can therefore be distinguished directly in the SDS gel. Despite cleavage, the fragments cosediment into the CLP-specific gradient fractions.

This example demonstrates that CLPs composed of core protein with an inserted 65 aa peptide (linker+ACID+TEV cleavage site) can also be cleaved specifically, while retaining the particulate structure nevertheless.

EXAMPLE 3

Another example shown is a corresponding experiment using a core protein containing the aa sequence 18-273 of the *Borrelia burgdorferi* OspA protein. The corresponding protein without TEV cleavage site is described in Nassal et al., 2005; only a fraction of it formed regular particles, and these results were evident in a broad distribution in the sucrose gradient. The uncut vaccine as such can thus be used only to a limited extent. Moreover, this uncut vaccine would not be applicable in humans/medically, since very long extra linker sequences with an intrinsic, undesired antigen potential were required in order to obtain at least a small proportion of the preparation in the CLP form.

After introducing a TEV cleavage site, the fusion protein was treated with TEV protease as in example 2 and then sedimented in the sucrose gradient. Here too a specific cleavage occurred which, however, was not complete (presumably due to steric hindrance via OspA, poorer accessibility of the TEV cleavage site); classification of the fragments by means of monoclonal antibodies which specifically recognize the N-terminal or C-terminal core moiety; consequently, the a-coreN antibody reacts with the uncleaved fusion protein and the N-terminal cleavage fragment. The partially cleaved material nevertheless exhibited a particle-typical migration behavior. These data indicate that particle formation was markedly improved by opening either of the two connections between inserted foreign protein and core carrier.

This example proves that a core fusion protein with a large foreign protein insertion (255 aa OspA+linker+TEV cleavage site) can be cleaved specifically (albeit less efficiently). While the previously described continuous core OspA fusion protein is distributed broadly across the gradient (Nassal et al., 2005), the (partially) cleaved fusion protein is distinctly concentrated in particle-typical gradient fractions. This is an indication of the efficiency of particle formation being improved by cleavage.

A further experiment demonstrated that coexpressed (from a compatible plasmid) TEV protease cleaves core fusion proteins carrying TEV cleavage sites, sometimes more efficiently than is possible by subsequent in vitro cleavage. Particle formation was also detected, via sucrose gradient sedimentation, for the fusion proteins which had already been cleaved in the bacteria.

Examples 1 to 3 demonstrated that preformed CLPs remain intact after cleavage in the region of the c/e1 epitope. This may be explained structurally by the fact that the connecting loop between the spike-forming helices has no structural role per se but could not have been expected in this way. This led to the more preferred embodiment in which, instead of subsequent cleavage of the continuous protein chain, the coreN and coreC parts are expressed directly as separate protein fragments, during which process they obviously come together spontaneously and form particles. Such an approach has at least three substantial advantages:

(i) Simplification: the additional cleavage step with TEV (or a different) protease is no longer necessary;
(ii) no additional peptide sequence in the fusion protein is required for specific protease recognition;
(iii) a particle formation, even if only partial, with a sterically unfavorable foreign protein such as OspA required very long linker sequences; this can be dispensed with, if steric hindrances were avoided because the linkage on both sides with the core carrier protein would no longer be required.

Points (ii) and (iii) are important in particular for vaccine applications because any additional sequence may result in unpredictable immunological consequences (new epitopes due to the additional sequences, possibly cross reactions with endogenous epitopes).

EXAMPLE 4

Expression Constructs for Approximately Equimolar Expression of coreN and coreC Fragments The continuous peptide chain contains inevitably equimolar amounts of the later cleavage products. With separate expression, the two parts should therefore likewise be produced in approximately equimolar amounts for efficient assembly. In first experiments, two separate, compatible plasmids were employed for expressing the two carrier protein parts, but with only moderate success.

In a preferred embodiment, bicistronic vectors are employed which moreover have the advantage that a selection with another antibiotic (for retaining the otherwise necessary second plasmid) can be dispensed with.

Type 1 constructs include downstream of a shared promoter (here T7 phage RNA polymerase promoter) two expression cassettes having in each case an upstream ribosome binding site (RBS; Shine-Dalgarno sequence). In the vectors provided here, translation of the coreN fragment is stopped by an artificial stop codon downstream of aa proline 79 (P79), and an artificial start codon upstream of aa serine 81 (S81) enables translation of the second fragment to be initiated. An operon structure of this kind can often be found in bacteria ("polycistronic mRNAs"; ribosomes may bind to each RBS on the mRNA relatively independently and initiate translation of the gene located 3'). In the constructs provided, the second RBS is an exact copy of the first RBS which is derived from the original pET vectors; other RBS sequences are certainly likewise possible. The ATG start codon of the second cistron is part of an Nde cleavage site (CATATG) for easy cloning of foreign sequences.

Type 2 constructs ("stop/start") do not contain a separate second RBS; rather, an initiation codon for the downstream gene (NNA TGA) overlaps with the stop codon of the upstream gene (NNN TGA) in a reading frame shifted by 1. In this case, ribosomes can read the first gene and then directly reinitiate at the ATG of the second gene; such an arrangement enables two genes to be coexpressed; similar stop-start arrangements can be found in some bacterial phages. Said arrangement is also implemented in some eukaryotic non-LTR retrotransposons (ORF1/ORF2 junction). On the basis of the known sequences, for example in the *E. coli* Trp operon, other combinations of adjacent or overlapping stop/start codons (e.g. TA<u>ATG</u>, TG<u>ATG</u>, etc.) should be equally suitable.

Preferred expression vectors are depicted diagrammatically in FIG. 3.

Top: Type 1 constructs. A promoter, for example for T7 RNA polymerase, results in transcription of a bicistronic mRNA (a terminator sequence may be inserted 3' for efficient termination). The first cistron encodes the HBV core protein aa sequence 1-79. An upstream ribosome binding site (RBS1) enables translation to be initiated (small and large ribosomal subunits depicted as ovoids). A stop codon is located downstream of the 3' end of the codon for P79. Another RBS (RBS2), for translation initiation of the coreC fragment, is located at the 5' end of the second cistron. This fragment additionally possesses its own initiation codon (ATG). In the example shown, the coreC sequence starts with Ala80 and may extend to aa position 140, better 149, or to the authentic end, at position 183. The aa sequence from position 140, better 149, onward may also be replaced with foreign sequences.

Bottom: Type 2 constructs. These contain only a single RBS upstream of the first cistron. Translation of the coreC fragment is carried out by reinitiation, with the artificial start codon of coreC (ATG) overlapping with the stop codon of coreN (TGA), as shown. In the example, the coreC sequence starts with Ser81. aa 77, 78 and 79 of the core protein are glutamate (E; codons: GAA, GAG), aspartate (D; codons: GAC or GAT), aa 79 proline (P; codons: CCN). In the type 1 constructs provided, the nucleotide sequence GAG GAT CCN was chosen for the aa sequence EDP, which generates a BamHI cleavage site (GGATCC); this unique BamHI cleavage site makes possible the simple cloning of different coreN- and coreC-encoding DNA fragments. The nucleotide N in the proline codon CCN is not defined; the stop codon may be TAA, TAG or TGA.

The sequence up to the end of the first gene in type 2 constructs is GGATCCa TGA (SEQ ID NO: 3). This sequence also contains a BamHI cleavage site (underlined) for cloning different coreN- or coreC-encoding DNA fragments. P79 in the type 2 constructs provided must have the codon CCa and the stop codon must be TGA (>CCaTGa) to allow an overlapping ATG initiation codon for the second gene to be generated. The codon for the first aa of the second gene after the ATG start codon must start with A. Alternative stop/start nt sequences would be TGATG or TAATG, as in the *E. coli* Trp operon between TrpE and TrpD or else TrpB and TrpA [Das and Yanofsky (1989), Nucl. Acids Res., pp. 9333-9340; Oppenheim and Yanofsky (1960), Genetics, pp. 785-795].

The backbone of the vectors provided (pET28a2-xxx) is based on the commercial vector pET-28 in which, however, the kanamycin resistance gene has been replaced with that of ampicillin resistance. It is certainly possible, however, to apply also other vector backbones (different origins of replication, different resistance genes, different promoters, different RBS). The bicistronic arrangement of the genes for coreN and coreC, either by way of two separate RBS or by way of stop/start arrangement, is essential. In our own experiments it was possible to express multiple split-core proteins both from type 1 and from type 2 constructs, although the number of type 2 (stop/start) constructs where this was the case was smaller. In addition, there is less possible sequence variability in type 2 constructs (see above). Type 1 constructs are therefore more widely applicable.

The chosen C-terminal aa of the coreN moiety was P79 because proline is particularly protease-resistant and degradation of the fragment is thus minimized. Owing to the known 3D structure and to described deletion variants in this central region, it can therefore be assumed that (i) the end of the coreN fragment could be located in the region of the aa from approx. position 72-74, particularly Gly73, (ii) the start of the coreC fragment could be located in the region of the aa from approx. position 78-86, possibly up to Gly94, without substantially different results than those using the limits chosen here (coreN end at P79, coreC start at S81, with upstream start ATG) being obtained.

Owing to the different transcription and translation mechanisms, the constructs described cannot be applied in this form for expression in eukaryotic cells; a eukaryotic promoter rather than the prokaryotic promoter must be used (e.g. CMV-IE and many others), and a polyadenylation signal (for example from SV40 virus or many others) must be introduced downstream of the end of the open reading frame(s).

Approximately equal expression of coreN and coreC in eukaryotes can be achieved by:

(i) cotransfection of two plasmids (one each for coreN, one for coreC);

(ii) transfection of a plasmid with two independent expression cassettes;

(iii) transfection of a plasmid with functionally bicistronic mRNA; for example, the second gene could be expressed by an upstream internal ribosome entry site (IRES);

(iv) a type 2 vector-like stop/start arrangement may also be functional in eukaryotes.

EXAMPLE 5

Separate Expression of wt coreN and coreC Fragments Produces Intact CLPs

Wild-type core protein was expressed in two parts by means of expression vectors based on type 1 (FIG. 3) in *E. coli* BL21 cells, in one case on the basis of aa 1-149, in the other case on the basis of aa 1-183. Both expected fragments were produced and assembled to give intact CLPs. This was detected using sucrose gradients and native agarose gel electrophoresis. The formation of CLPs was detected directly by carrying out an electron-microscopic comparison (negative staining) of particles composed of the continuous aa 1-183 chain with C-terminal His6 tag versus particles composed of the corresponding split-core system. No differences were detectable at this resolution.

Wt-HBV CLPs are very robust and resistant to molar concentrations of urea; CLPs composed of C-terminally truncated core protein 1-149 can be dissociated into dimers by 3-5 M urea and reassociated again to CLPs in vitro by changing the buffer conditions (removing the urea, neutral pH, increased salt concentration). A comparative study on the stability of the CLPs composed of split-core demonstrated a similarly high stability of split-core CLPs. This indicates the high affinity of the coreN and coreC moieties for one another and is important for the use as carrier system for foreign molecules.

EXAMPLE 6

Separate Expression of Foreign Protein-Fused CoreN and wt-coreC Fragments, and Vice Versa, Produces Intact CLPs GFP fused to either coreN or coreC was used as model for proving, that the split-core system is suitable in principle for CLP formation and presentation of foreign proteins; either a type 1 (second RBS) or a type 2 (stop/start) vector was utilized for the coreN construct. All constructs resulted in expression of green fluorescent proteins which formed particles, according to sedimentation in sucrose gradients.

In order to further prove physical association of the particular coreN and coreC fragments, aliquots of the gradient fractions were subjected to electrophoresis in native agarose gels. In this case, particles remain intact, as does the GFP chromophore. The fractions of both GFP on coreN and GFP on coreC produce a distinct, green fluorescent band; unassembled GFP fusion protein remained in the upper gradient fractions and displayed a different migration behavior and a more diffuse distribution (more rapid diffusion in the gel due to the substantially smaller structure in comparison with particles composed of 180 or 240 subunits). CoreC was also detected by the α-coreC antibody in the green fluorescent (i.e. GFP-containing) band, both for GFP on coreN and for GFP on coreC.

This example demonstrates two things, namely
(i) In the split-core system, a foreign protein of approx. 240 aa, in this case GFP, can be fused both to coreN and to coreC, without interfering with CLP formation.
(ii) Both type 1 and type 2 split-core vectors are suitable for coexpression of coreN and coreC with foreign sequence attached thereto by fusion.

EXAMPLE 7

CLP Presentation of Medically Relevant Foreign Proteins in the Split-Core System, which is not Possible, or is Possible Only to a Very Limited Extent, by Conventional Means

*Borrelia burgdorferi* OspA

As explained at the outset, linking the inserted foreign protein on both sides to the carrier protein, which is required in the previous system, results in great topological restrictions. In contrast to GFP, OspA does not have a natural "fit". OspA was therefore used as a precedence for an unfavorably structured foreign protein in the split-core system and fused to either coreN or coreC. In contrast to the earlier continuous construct [described in Nassal et al., 2005] with broad distribution in the gradient, both fusion proteins accumulated distinctly in the particle-typical fractions. An analysis by electron microscopy demonstrated a drastically improved efficiency of CLP formation, both for the fusion of OspA to coreN and for the fusion of OspA to coreC, compared to the old, continuous construct.

This example proves that
(i) the split-core system allows foreign proteins whose structure interferes with CLP formation in the conventional continuous-core system to be presented as CLPs,
(ii) the split-core system enables CLPs to be formed efficiently by fusion of the foreign protein both to coreN and to coreC.

Similarly it was also possible to present *Borrelia burgdorferi* OspC successfully in the split-core system of the invention.

EXAMPLE 8

Circumsporozoite Protein of the Malaria Pathogen, *Plasmodium falciparum*

Another pathogenic protein highly relevant in view of vaccines is the circumsporozoite protein (CSP) of the malaria pathogen, *Plasmodium falciparum*. CSP (form used herein: total length of 319 aa) contains an approx. 110 aa repeat of the tetrapeptide motif NANP/NVDP (SEQ ID NOS 11-12, respectively, in order of appearance). The structure of CSP is not known; the approx. 50 aa C-terminal domain with 4 Cys residues is probably (based on sequence homology) folded similarly to thrombospondin type 1 repeats. Although the repeat is immunogenic, the other CSP regions possibly also contain important epitopes. It has not been possible to prepare full-length CSP in the CLP form using the conventional continuous-core system, whereas this was very readily achieved using the split-core system. Unambiguous data are currently available for fusion of CSP to coreN; coexpression with coreC (both as 149 and as 183 construct) produces efficiently particulate structures.

A series of constructs (based both on core 1-149 and on 1-183) was prepared) which contain either only the repeat sequence or truncated CSP without Cys-rich domain, in each case in the continuous- or split-core system; in addition to this, complete CSP fused to coreN. The CLP preparations were used in a comparative immunogenicity study in mice, which, however, has not been concluded yet. The data so far indicate that the vaccine prepared in the split-core system has superior properties. This can be attributed to the fact that the complete CSP is capable of forming CLPs only when the carrier system of the invention is applied. In contrast, other systems do not produce any CLPs. As a result, CSP vaccines prepared with the aid of the carrier system of the invention should have superior immunogenicity and induce in particular neutralizing antibodies.

EXAMPLE 9

Split-Core CLPs as Carriers for Foreign Proteins Enhance B-Cell Response to Foreign Protein In an immunogenicity study in mice, 5 core-OspA constructs of the split-core system are compared to lipidated OspA (LipOspA) which has not been fused to a core; the commercial Lymerix vaccines are based on this and are therefore the current "gold standard" of Lyme disease vaccines. The lipid moiety in LipOspA (tris-palmitoyl-cystein-(Pam3-Cys)) is essential for its relatively high immunogenicity, non-lipidated OspA being only very weakly immunogenic (cf. Nassal et al., 2005). Three of the core-OspA constructs contain full-length OspA (aa 18-273), and another two contain truncated OspA (starting at aa 185, to aa 273).

For this purpose, 6 groups of in each case 5 BALB/c mice were immunized 4 times with in each case 10 μg of antigen (days 0, 14, 29, 49):
Group 1: LipOspA
Group 2: Full-length OspA (aa 18-273) on coreN, coreC from core aa 81 to 183
Group 3: Full-length OspA (aa 18-273) on coreN, coreC from core aa 81 to 149
Group 4: Truncated OspA (aa 185-273) on coreN, coreC from core aa 81 to 183
Group 5: Truncated OspA (aa 185-273) on coreN, coreC from core aa 81 to 149
Group 6: Full-length OspA (aa 18-273) on coreC to core aa 183, coreN from aa 1-79.

The induced antibodies were determined by taking blood on day-1 (=1 day before the first immunization; =preimmune serum), and on days 8, 26, 36 and 57. The following were determined by means of ELISA: the kinetics of production of OspA-specific antibodies; the particular proportion of LA2-equivalent antibodies, LA2 being a monoclonal antibody which is known to be neutralizing and which recognizes a complex conformational epitope of discontinuous aa sequences downstream of aa 185 of OspA.

The results of this experiment are depicted in detail in FIG. 4.

FIG. 4A depicts the kinetics of induction of total anti-OspA antibodies (in μg of specific Ab per ml of serum). The sera of mice immunized with the full-length OspA split-core constructs contain detectable anti-OspA titers even after the second immunization which are comparable to those caused by LipOspA. After the 3$^{rd}$ and 4$^{th}$ immunizations, the anti-OspA titers in the mice immunized with split-core full-length OspA markedly exceed those of mice immunized with LipOspA; the titers are particularly high after immunization with OspA18-273 to coreC (group 6). Truncated OspA185-273 in the context of core149 (group 5) and core183 (group 4) elicits only a substantially lower OspA-specific response.

FIG. 4B compares directly the total anti-OspA Ab titers with those directed to the known neutralizing LA2 epitope in the C-terminal region of OspA. Full-length OspA on coreN, in the context of both core149 and of core183 (groups 2 and 3, respectively), induce higher anti-LA2 equivalent Ab titers than LipOspA, with full-length OspA on coreC producing markedly lower titers. A study on the particular neutralizing Ab content (protection to challenge with the *B. burgdorferi* pathogen) is continued.

The example demonstrates that split-core CLPs induce specific antibodies to the full-length OspA foreign protein presented, with the titers being higher than with the established lipidated LipOspA in which the lipid moiety is essential for immunogenicity. The different proportion of LA2-equivalent Ab after immunization with OspA on coreN (approx. 30%) versus OspA on coreC (<5%) demonstrates that the type of linkage affects the type of Abs produced; for this, see example 10.

EXAMPLE 10

Specific Induction of Region-Specific Antibodies to a Foreign Protein by Alternative Fusion Either to coreN or to coreC With proteins whose N and C termini are not in immediate proximity to one another like in GFP, fusion to coreN results in a different orientation with respect to the particle surface than fusion to coreC (coreN: C-terminus of the foreign protein "out"; coreC: N terminus of the foreign protein "out"). When used as B cell vaccines, those protein moieties which extend in each case furthest into the solvent can be expected to elicit the strongest antibody response. Therefore different region-specific antibodies can be induced by fusing the foreign protein either to coreN (C-terminal side of the foreign protein "out") or to coreC (N-terminal side of the foreign protein "out").

FIG. 5 depicts diagrammatically a possible way of determining for a foreign protein with an elongated structure, such as OspA herein, via fusion to either coreN or coreC, the part of the molecule which faces furthest away from the CLP surface. A well-mapped epitope in OspA is LA2, in the C-terminal region, which is recognized by a neutralizing monoclonal antibody, LA2. As expected, split-core OspA CLPs with OspA on coreN (the OspA C terminus is therefore exposed) induced a strong LA2-equivalent response, with CLPs with OspA on coreC inducing only a weak LA2-equivalent response. Instead, the response to other regions of OspA is enhanced.

A fusion of OspA as foreign protein to coreN was expected to provide good access to the LA2 epitope in the C-terminal OspA region, whereas a fusion to coreC was expected to provide good access to the N-terminal OspA region which had not been well characterized immunologically thus far. The data depicted above impressively confirm this concept (very high anti-total OspA titers but only low LA2-equivalent Ab titers for OspA on coreC).

The split-core system thus has a high immune-enhancing activity, with both fusion of the foreign protein to coreN and fusion of the foreign protein to coreC.

The type/region specificity of the induced antibodies can be controlled by choosing the linkage site (coreN vs coreC). For optimal vaccination results, mixtures of split-core vaccines may be employed in which one part of the heterologous foreign amino acid sequence is fused to the coreN moiety and the other part to the coreC moiety, so as to achieve optimal presentation of various epitopes.

EXAMPLE 11

Fusions with Significance Beyond Vaccine Applications

Apart from direct significance as immune-enhancing particulate carriers for peptide, and here in particular protein, antigen vaccines, a multiplicity of further applications for such a carrier platform are conceivable. In each case, a large number (180 or 240) of presented molecules are brought into close, symmetric proximity to one another. If said molecules are interaction-capable foreign molecules (vaccines are a special case: interaction with antibodies), the particle having multiple copies of the foreign molecule has a drastically increased avidity, compared to the monomeric foreign molecule (cf. natural IgM pentamers; also MHC tetramers in immunodiagnostics). Such interaction-capable foreign molecules must be accessible on the CLP surface in order to be able to react with their interaction partners. The split-core system facilitates this substantially, compared to the conventional continuous system.

A number of model foreign sequences were expressed in the split-core system and all insertions assayed formed CLPs. The interaction capabilities of some of them were detected directly.

The split arrangement enables new termini to become accessible on the CLP surface for further derivatization. FIG. 5 depicts a split-core dimer with an ACID peptide fused to coreN, which peptide can interact with the complementary BASE peptide. A molecule X to which said BASE peptide has been fused binds to the ACID CLPs. The split arrangement renders ACID flexible; ACID inserted in the continuous core system interacts with the BASE peptide but, since the ACID and BASE peptides form a rigid coiled-coil double helix [O'Shea et al., 1993], the structure of the core carrier becomes unstable and the CLPs disintegrate. In the split arrangement, however, the CLPs should remain stable. This coupling can be generalized: a different interaction-capable molecule A than the ACID peptide may be fused to coreN or coreC. Corresponding CLPs may then interact with B, a specific interaction partner of A. Such interaction partner pairs are His6-Ni-NTa ("His6" disclosed as SEQ ID NO: 4), biotin acceptor peptide—streptavidin; Z33—immunoglobulin.

Other possible couplings are explained in more detail below:
a) His6 Tag ("His6" Disclosed as SEQ ID NO: 4):
Fused to coreN via Gly2 linker; forms particles which bind to Ni2$^+$NTA agarose. His tag is freely accessible, in contrast to the continuous system. A comparable insert (His7) ("His7" disclosed as SEQ ID NO: 5) in c/e1 of the continuous-core system do not produce any significant amounts of protein because the His6 tag ("His6" disclosed as SEQ ID NO: 4) residue is not sterically accessible there.

b) Biotin Acceptor (BA) Peptide:

Biotin acceptor (BA23) is an artificial 13 aa peptide (GLN-DIFEAQKIEWH) (SEQ ID NO: 6) which is biotinylated by *E. coli* biotin ligase, BirA. Efficient biotinylation requires free accessibility which is provided in the split-core system but not, or only to a limited extent, in the continuous-core system. The split-core-BA fusion protein forms CLPs and is biotinylated in *E. coli*. Avidin/streptavidin or their conjugates can be bound to the CLP-presented biotin.

c) Z33 Domain of Protein A (SEQ ID NO: 17):

*S. aureus* protein A binds immunoglobulins with high affinity ("protein A sepharose" for immuno-precipitation). Protein A consists of 5 structurally similar Ig-binding domains. Z33 constitutes a single one of such domains with a modified aa sequence; total length: 33 aa). Z33 still has high affinity for Ig's (Kd 40 nm). Binding to different Ig's requires structural flexibility and, moreover, accessibility. The Z33 sequence was fused via a long linker sequence to coreN:

*GGGGSGGGVEDGGGGSGGGGT*-FNMQQQRRFYEALHDPNLNEEQRNA

KIKSIREDP (SEQ ID NO: 70).

CLPs formed in the split-core system. After adding an FITC-labeled immunoglobulin and precipitating again, a proportion of the fluorescence was detected in the particle-typical gradient fractions. This was not the case, if wt-core protein CLPs rather than the Z33 fusion were used.

d) ACID Peptide Insert:

The ACID peptide (SEQ ID NO: 19) inserted in the continuous-core system interacts with the complementary base peptide ("peptide Velcro") via coiled-coil formation of the peptides; [O'Shea et al., 1993], with massive modifications to the core structure up to its disintegration; this is caused by the ACID peptide on its own adopting a flexible structure which does not put any stress on the core structure. Addition of the BASE peptide (SEQ ID NO: 20) results in interaction with the ACID sequence, as a result of which both peptide sequences adopt a rigid helical coiled-coil conformation. Tension arises due to the linkage on both sides. An ACID peptide fixed only on one side should be able to interact without tension with added BASE peptide or BASE peptide fused to further partners. In any case, the particle structure of the ACID fusion protein in the conventional continuous-core system remains intact after cleavage of the C-terminal connection to the core carrier by means of TEV protease.

Split cores with exposed ACID sequence may be charged with foreign proteins to which the complementary BASE peptide is coupled. This is one of several possibilities of charging split-core CLPs later with foreign molecules of choice.

The coupling mechanisms detailed above enable CLPs having one part of the coupling to be provided. The protein fused to the other part of the coupling may readily be coupled to said CLPs. In this way it is possible, for example, to present to the immune system non-peptide-like structures.

e) Simultaneous Fusion of Different Foreign Molecules to coreN and coreC

In the previous examples, in each case one foreign sequence was fused to either coreN or coreC. In principle it is also possible to fuse two different foreign molecules to coreN and coreC simultaneously; a possible example of these are the two subunits of a heterodimeric foreign protein. The model utilized was a two-part GFP, the first segment of which, containing the first 10 of the 11 GFP β strands, was fused to coreN and the second segment of which, containing the 11$^{th}$ GFP β strand, was fused to coreC. Coexpression from a type 1 vector produced green fluorescent CLPs. Thus the coreN and coreC domains had assembled to give an assembly-capable CLP structure and the two GFP parts had supplemented each other to give a correct 3D structure with formation of the GFP chromophore.

The example demonstrates that simultaneous fusion of different foreign sequences to coreN and coreC with formation of functional structures of both the split-core carrier and the two different foreign sequences fused to coreN and coreC is possible.

EXAMPLE 12

Split-core CLPs which Present the GB1 Domain of Protein G on the Surface

Another specific example involved introducing the "GB1" domain (SEQ ID NO: 18) of the *Streptococcus* spp. immunoglobulin-binding protein "protein G", which is functionally related to protein A, into the HBV split-core system. Protein G likewise consists of multiple similar domains. Like protein A, protein G binds to immunoglobulins but has different specificities with regard to IgG species origin and subtypes. Due to this complementarity of protein G and protein A, both are commercially available as reagents for immunological detection assays based on binding to different immunoglobulins. Like protein A, protein G and the GB1 domain derived therefrom also binds the constant (Fc) part of the antibody, with the variable, antigen-recognizing part of the antibody remaining accessible for binding to the antigen. Thus it is possible to bind a multiplicity of different antibodies.

In this example, the GB1 domain was introduced into the split-core system, and it was demonstrated that (i) CLPs are formed and (ii) that these CLPs—but not control CLPs without GB1—are capable of binding different antibodies.

In a manner similar to the examples mentioned above, the GB1 domain was genetically fused to coreN or to coreC and coexpressed with the respective missing coreC and coreN fragments.

The specific aa sequence corresponds to aa 229 to 284 of the protein G precursor protein (Swiss Prot Accession; P06654); the 3D structure is known (PDB Accession: 1PGA; Ref: Gallagher T, Alexander P, Bryan P, Gililand G L (1994) Two crystal structures of the B1 immunoglobulin-binding domain of streptococcal protein G and comparison with NMR Biochemistry 33: 4721-4729) coreD78-GGGGSGGGGTQ-YKLILNGKTLKGETTTEAVDAA-TAEKVFKQYANDNGVDGEWTYDDATKTFTVTEd P (SEQ ID NO: 8)

Linkage to coreN was via a G4SG4TQ linker(SEQ ID NO: 9); the second last aa, K, was replaced with D (in lower case in the sequence); the downstream E residue is the last aa visible in the X-ray structure; the K>D substitution enables a BamHI cleavage site to be introduced at the nucleotide level (Gag gat cct TAG) (SEQ ID NO: 10); the latter is therefore in a position homologous to the constructs described above.

As in the other examples, particles were formed in an efficient manner, and this was detected by sucrose gradient sedimentation, migration behavior in a native agarose gel and by electron microscopy.

The interaction capability of the CLP-carried GB1 domains was detected by incubating the particles with immunoglobulins and then sedimenting again in a sucrose gradient; in the process, the antibodies clearly co-sedimented with the particles. IgG binding was also detected by the fact that the coreN-GB1 fragment reacted directly with secondary antibody conjugates on Western Blots after SDS gel electrophoresis. The modified GB1 was therefore, even in the context of fusion to coreN capable of renaturing efficiently and binding to its ligand, IgG.

To prove that the particle-bound GB1 indeed binds immunoglobulin, an aliquot of the corresponding sucrose gradient fraction was incubated with a 5 nm gold-labeled antibody, unbound antibody was removed by sedimenting again in a sucrose gradient and the particle fraction was analyzed by electron microscopy. The electron-dense gold particles indicated binding of the antibody to intact CLPs.

EXAMPLE 13

Self-Fluorescent GFP- and GFP Variant-Containing Split-Core CLPs which Present Interaction-Capable Foreign Molecules Example 11 e) illustrates fusions having significance beyond vaccine applications, with a GFP molecule in two parts (GFP β1-10 and GFP β11) associating when GFPβ1-10 is fused to coreN and GFPβ11 is fused to coreC, producing the native GFP structure (green fluorescence) and forming CLPs.

In the present example, additional foreign sequences were fused to GFPβ11, namely the GB1 domain of protein G and the preS domains of the surface proteins of human HBV, duck HBV and heron HBV. This is possible only because the split arrangement produces a new N terminus on GFPβ11, which moreover faces outward from the CLP surface, due to the specific orientation on the split-core CLPs. The particular expression plasmids were constructed, in a manner similar to the methods described above, in split-core vectors coding for separate coreN and coreC fragments, in this case already linked by GFPβ1-10 to coreN and GFPβ11 to coreC.

It had been expected on the basis of previous data that the N terminus of the GFPβ11 segment would face outward, away from the CLP surface, and the presence of another foreign domain would therefore not interfere in principle with the ability of the coreN and coreC moieties to form a particle structure, nor with the ability of the GFPβ1-10 and GFPβ11 moieties to form the native GFP structure. The result of this example is depicted diagrammatically in FIG. 7. Parts A-D of this figure depict the following:

A. Basic structure of the two parts of the fusion protein. GFPβ1-10 is fused to coreN, GFPβ11 is fused to coreC. Since GFPβ11 provides a new N terminus, another domain, here GB1, can be fused to the latter. B. Self-fluorescent CLPs are produced by coreN interacting with coreC (CLP formation), and GFPβ1-10 interacting with GFPβ11 (formation of the GFP chromophore), as has been shown previously. In addition, however, they present GB1 in an accessible form on their surface. C. Different antibodies can be bound via their Fc part to the GB1 domains. D. The antibodies for their part can interact via their different variable parts with their specific antigen. Split-core GFP-GB1 CLPs can thus replace the usual fluorescently labeled secondary antibody in indirect immunofluorescence. FIG. 7 depicts an application to fluorescent labeling of tubulin in two different cells. Other applications based on antibodies binding to antigen are similarly feasible.

It was indeed possible to coexpress the further modified fragments efficiently in E. coli where they formed CLPs, according to sedimentation in a sucrose gradient and migration behavior in a native agarose gel. In addition, these CLPs exhibited typical GFP fluorescence and thus the GFP moieties had also come together in the correct manner. The example indicates that the GB1 moieties were also correctly folded and accessible on the CLP surface.

The ability of the self-fluorescent GB1-presenting CLPs to bind to antigen-bound antibodies was detected by permeabilizing HeLa (human) or LMH (chicken) cells which were then incubated with a mouse primary antibody to tubulin. In one case, the cells were incubated conventionally with a chemically fluorescently labeled (Cy2) secondary antibody (goat anti-mouse), or alternatively with the self-fluorescent, GB1-presenting split-core CLPs, and then washed; finally, the cells were observed by fluorescence microscopy.

In both cases, comparable fluorescence images were obtained (as expected, cytoplasmic staining, leaving out the nucleus). Thus, the GB1 domains must have been capable of binding to the anti-tubulin primary antibodies bound to tubulin.

Self-fluorescent split-core CLPs which present GB1 may thus be employed as an alternative to conventional fluorescently labeled secondary antibody conjugates for detecting an antigen-bound primary antibody. This proves that the GB1 domains are still capable of interacting with IgG and that they therefore must be correctly folded. Moreover it proves that the self-fluorescent, GB1-presenting CLPs can be employed as a general detection reagent (comparable to a fluorescently labeled secondary antibody).

Similar constructs were obtained with color variants of GFP, in which constructs known mutations which alter the absorbance and emission spectra were introduced into the present GFP construct by directed mutagenesis. Specifically, yellow fluorescent protein (YFP) and cyan fluorescent protein (CFP) variants were prepared. Both variants formed CLPs which in each case exhibited the typical absorbance spectra. Thus it is possible to generate GB1-presenting split-core GFP CLPs having different chromophoric properties, which are suitable for multi-immunofluorescence applications.

The split-core system allows preparation of self-fluorescent CLPs which present an interaction-capable further foreign molecule on their surface. This foreign molecule, if it is GB1, is still capable of interacting specifically with immunoglobulins, even when these are bound to their target antigen. As a result of this, there is a new possible application which goes beyond vaccine applications, namely direct detection, via fluorescence, of different antigens by means of the self-fluorescent CLPs. Such self-fluorescent, interaction-capable split-core CLPs are particularly suitable for diagnostic and analytical applications.

Self-Fluorescent Split-Core CLPs which Present Foreign Domains of Protein G Other than GB1

The results above indicate that a further foreign domain, GB1, may be presented in a functional form, i.e. capable of interacting with the specific ligand, IgG, on split-core CLPs which additionally contain a two-part GFP. GB1, with fewer than 60 aa, is a relatively small domain, however. In order to prove generalizability, homologous constructs were prepared in which GB1 with the preS domains of the large envelope proteins of human (HBV), duck (DHBV) and heron (HHBV) HBVs. These domains mediate specific binding of the respective viruses to their natural target cells, i.e. hepatocytes of the corresponding host species. With 108 aa in HBV and approx. 160 aa in DHBV and HHBV, the preS domains are distinctly larger than GB1 and moreover their sequences are different from GB1 but also from each other.

All three domains were inserted in split-core-GFP fusion proteins in a manner similar to GB1 (cf. FIG. 7; replace GB1 with the corresponding preS domains). All three of them efficiently formed CLPs, as was detected by sucrose gradient sedimentation, migration behavior and native agarose gel electrophoresis and by electron microscopy; the CLPs exhibited typical GFP fluorescence (i.e. the GFP moieties had associated to give the correct 3D structure of GFP); moreover, the HBV-preS and DHBV-preS CLPs reacted with monoclonal antibodies to HBV preS and DHBV preS; a corresponding antibody to heron virus preS is currently not available.

Another application comprises identifying the cellular receptors for the particular viruses. Due to the large number (240) of preS domains per particle, the CLPs can be assumed to have an enormously increased avidity for said receptors, thereby enabling the latter to be bound in a stable manner and also to be identified in this way. Receptor-carrying cells would be identified via GFP fluorescence of the CLPs by means of fluorescence microscopy or FACS; solubilized receptor molecules from such cells would be incubated with the CLPs and should then accumulate in the particle-typical gradient fractions in a subsequent sedimentation in sucrose gradients.

EXAMPLE 14

Split-Core OspA CLPs with OspA on coreN Generate Higher Titers of Protective anti-OspA Antibodies than LipOspA, Split-Core OspA CLPs with OspA on coreC Generate Lower Titers As FIG. 5 shows, the orientation of a presented foreign protein can be influenced in a targeted manner by linkage to either coreN or coreC. In the case of OspA, this results in particularly good exposition of either the C-terminal epitope of the monoclonal antibody LA-2 which is known to be neutralizing (fusion to coreN) or the N-terminal OspA region which does not contain any known neutralizing epitopes (fusion to coreC). As FIG. 4 shows, both split-core-OspA CLPs (there: group 2 for coreN fusion and group 6 for coreC fusion) produced total anti-OspA antibody titers but the proportion of LA-2-equivalent antibodies is substantially higher with fusion to coreN—as expected from the structure.

However, the data here are in vitro data. In order to determine directly the protective potential of the induced antibodies in vivo, the ability of the particular immune sera to neutralize an artificially induced *B. burgdorferi* infection in an established mouse model was recorded (cf. Nassal et al., European. J. Immunol. 2005; pp. 655-665). SCID mice were inoculated i.p. with the appropriate immune sera, followed by an s.c. challenge with in each case $10^3$ spirochetes per mouse 2 hours later. This usually results in an infection in unprotected mice which manifests itself in arthritis-like symptoms which can be recorded semiquantitatively in the left and right tibiotarsal joints. A group of 3 mice which received only normal mouse serum served as negative control. Groups of in each case 6 mice which received either the purified monoclonal antibody LA2 which is known to be neutralizing or LipOspA-induced antibodies served as positive control. The test groups (likewise 6 animals each) received immune sera which had been produced due to split-core OspA with OspA on coreN or split-core OspA with OspA on coreC. In order to record quantitative differences, passive immunization was carried out first with 5 µg and then with 1 µg of La2 or of the volumes equivalent to these LA2 quantities of immune sera of animals vaccinated with LipOspA or with split-core OspA with OspA on coreN. The results are depicted in FIG. 8.

Due to the low proportion of LA2-equivalent antibodies in the immune sera produced by means of split-core OspA with OspA on coreC, equivalent volumes thereof to those of split-core OspA with OspA on coreN were used, regardless of the LA2-equivalent titer. Arthritis scores were determined on days 13, 17, 21, 28, 35, 45 and 52. The results for day 52 are summarized in FIG. 8.

As expected, all animals inoculated with normal mouse sera developed arthritis. Protection due to the monoclonal antibody LA-2 was reduced from 4/6 to 1/6 animals with dosis reduction from 5 to 1 µg, with 5/6 animals being protected by the LipOspA immune sera. Passive immunization with immune sera obtained via split-core OspA with OspA on coreN protected all (6/6) animals from infection, even at the low dosage. OspA on coreC had a markedly lower protective activity (4/6 animals at the high, 1/6 animals at the low dosage).

Split-core-OspA CLPs with OspA on coreN produce high titers of LA2-equivalent antibodies which are protective in vivo. The protective potential exceeds that of LipOspA-induced antibodies. Split-core-OspA CLPs with OspA on coreC induce high total titers of anti-OspA antibodies and only a small proportion of those is LA-2 equivalent, and they have only a lower neutralizing potential. Fusion of a foreign antigen to coreN thus causes an immune response which is quantitatively distinct from that of fusion to coreC.

EXAMPLE 15

Circumsporozoite Protein (CSP) of the Malaria Pathogen, *Plasmodium falciparum*

Full-length CSP in the split-core system induces an immune response which is stronger and broader than that of the immunodominant CSP repeat sequence in the conventional, continuous-core system.

The complete CSP, with a length of 319 aa, had been shown previously to be expressible only in the split-core system with CLP formation; this was not possible in the conventional continuous system. Although it was possible to prepare a truncated version without the cystein-rich C-terminal domain (CSPshort hereinbelow) also in the conventional continuous system, the protein showed a pronounced tendency to precipitate after a few days—this did not occur in the split-core system, which is evidence for superior protein-chemical properties.

A specialty of CSP is the presence of a multiple repeat of the tetrapeptide motifs NANP (SEQ ID NO: 11) and NVDP (SEQ ID NO: 12) (24 NANP (SEQ ID NO: 11) and 3 NVDP (SEQ ID NO: 12) motifs in the full-length version utilized herein); said motifs are known immunogens, and an experimental vaccine based on the conventional continuous-core system has been described. A comparative immunogenicity study therefore involved preparation of a corresponding conventional construct in which the repeat sequence NANPN-VDP(NANP)$_3$NVDP (SEQ ID NO: 13) was located between core aa D78 and S81 and which formed CLPs—as expected, since the insert is small. Said construct was used in an immunogenicity study for comparison with full-length CSP and the C-terminally truncated CSPshort. Mice were immunized with in each case the same amounts of the particular CLPs (20 µg/mouse); the amounts of antibodies produced were determined by ELISA after 2, 4, 6 and 8 weeks; this was followed by a booster immunization (similar to the first one), and the titers were determined again 2, 4 and 6 weeks after the boost. Recombinant CSP (as fusion protein from *E. coli*), NANP (SEQ ID NO: 11) and NVDP (SEQ ID NO: 12) peptides and recombinant HBcAg were used as test antigens in order to determine the B cell response to the carrier. The antigens were immobilized on ELISA plates and then assayed using 2-fold serial dilutions of the immune sera. The highest possible dilution which gave a signal above the background is indicated in FIG. 9.

This results in the following conclusions:

a) B Cell Response to Recombinant CSP

All three immunogens resulted in extremely strong response to CSP; however, the response to full-length CSP is still 4 times higher (titer: 1:12×10$^6$ vs 1:3×10$^5$ for repeat and truncated CSP, respectively), meaning that a 12 million-fold dilution (!) of the immune serum is still capable of recognizing CSP protein.

b) B cell Responses to NANP (SEQ ID NO: 11) and NVDP (SEQ ID NO: 12) Repeat Peptides:

The responses to the NANP(SEQ ID NO: 11) peptide are similar for all constructs, as expected. The responses to the NVDP (SEQ ID NO: 12) peptide which is less common in the repeat are similar but are distinctly higher for the full-length CSP construct, even after the first immunization (without boost) (titer 1:2.5×10$^4$ vs 1:5×10$^3$).

c) B Cell Responses to CSP Sequences not Present in the Repeat:

Only CSPshort and full-length CSP induce a response to the peptides CSP12 (EEPSDKHIEQYLKKIQNSLS(SEQ ID NO: 14); pos. 246-264 in the full-length split-core construct) and CSP8 (GNGIQVRIKPGSANKPKDELD(SEQ ID NO: 15); pos. 274-294 in full-length split-core construct). The lack of corresponding responses after immunization with the repeat peptide in the continuous-core system is expected because the CSP8 and CSP12 sequences are not present there. The result is important in that specifically the full-length CSP can be produced only in the split-core system; using the split-core system, it is thus possible to address additional epitopes which may contribute to the protective action of a vaccination.

d) B Cell Responses to the Core Carrier:

Both CSPshort and full-length CSP in the split-core system result in an approx. 25-fold weaker response to the core carrier than the repeat peptide in the continuous system (titer 1:1.25×10$^5$ vs 3×10$^6$). Since the desired response to the foreign protein is at least as high as (CSPshort) or even higher than (full-length CSP) using the repeat peptide in the continuous-core system, specific immunogenicity with regard to the inserted foreign sequence is substantially improved when using the truncated, and in particular the full-length, CSP in the split-core system. In addition, a strong response to the core carrier makes differential diagnostics of anti-HBsAg-positive persons (infection vs anti-HBsAg by vaccination) more difficult; a low anti-core carrier response is therefore desired.

e) Full-Length CSP in the Split-Core System Activates T Cells

Induction of a T cell response was detected by stimulating splenic cells of the specifically immunized mice with rec. HBcAg or a known T-cell peptide (HBc 120-140) or with rec. CSP or the CSP peptides NANP (SEQ ID NO: 11) and CSP8, and then measuring IL-2 production. All constructs caused T cells to appear which were activatable by HBcAg, HBc120-140, rec. CSP and NANP(SEQ ID NO: 11). However, only splenic cells of mice immunized with full-length CSP in the split-core system were able to be stimulated by the CSP8 peptide to IL-2 production.

Therefore, the full-length CSP construct results in a broader response than the continuous only-repeat peptide construct also at the T-cell level.

The invention claimed is:

1. A split-core carrier system comprising the core protein of an hepatitis B virus (HBV), said HBV core protein having a three-dimensional structure characterized by two alpha-helices connected by loop region that comprises a c/e1 epitope, wherein said HBV core protein is cleaved at the loop region into two separate polypeptides: a core N domain polypeptide and a core C domain polypeptide, wherein at least one foreign molecule to which an immune response is to be elicited is fused to either the C-terminus of the core N domain polypeptide or to the N-terminus of the core C domain polypeptide, wherein the separate core polypeptides coordinate to form capsid-like particles like those formed by the uncleaved HBV core protein.

2. The split-core carrier system as claimed in claim 1, wherein said cure protein is from mammalian HBV.

3. The split-core carrier system as claimed in claim 2, wherein said core protein is from human HBV.

4. The split-core carrier system as claimed in claim 2, wherein said core protein is from woodchuck hepatitis virus (WHV).

5. The split-core carrier system as claimed in claim 1, wherein said foreign molecule is an amino acid sequence of a protein of a pathogenic bacterium.

6. The split-core carrier system as claimed in claim 1, wherein said foreign molecule is an amino acid sequence of a protein of a pathogenic eukaryote.

7. The split-core carrier system as claimed in claim 1, wherein said foreign molecule is an amino acid sequence of a protein of a virus.

8. The split-core carrier system as claimed in claim 1, wherein the foreign molecule is selected from the group consisting of:
   a) the sequence of the biotin acceptor peptide (SEQ ID NO: 6);
   b) the sequence of the ACID peptide (SEQ ID NO: 19);
   c) the sequence of the Z33 domain derived from protein A of *S. aureus* (SEQ ID NO: 17); and
   d) the sequence of the GB1 domain of protein G of *Streptococcus* spp (SEQ ID NO: 18).

9. A method of preparing a split-core carrier system for a foreign molecule as set forth in claim 1, said method comprising the steps of:
   a. providing an HBV core protein having a three-dimensional structure characterized by two alpha helices connected by loop region that comprises a c/e1 epitope;
   b. cleaving the HBV core protein at the loop region to generate two separated polypeptides: a core N domain polypeptide and a core C domain polypeptide; and
   c. fusing at least one foreign molecule to either the C-terminus of the core N domain or to the N-terminus of the core C domain, wherein the core domain polypeptides remain separated yet coordinate to form a capsid-like particle like that formed by the uncleaved HBV core protein.

10. The method as claimed in claim 9, wherein said foreign molecule is an amino acid sequence of a foreign protein.

11. The method as claimed in claim 10, wherein said amino acid sequence is at least 40 amino acids in length.

12. The method as claimed in claim 10, wherein said amino acid sequence is at least 120 amino acids in length.

13. The method as claimed in claim 10, wherein said two core domain polypeptides are expressed with the aid of a bicistronic vector, the first polypeptide comprising the core N domain and the second polypeptide comprising the core C domain, and the heterologous protein sequence being fused either to the C terminus of the core N domain or to the N terminus of the core C domain.

14. A medicament comprising the split-core carrier system as claimed in claim 1.

15. The medicament as claimed in claim 14, wherein said medicament is a vaccine.

16. A diagnostic agent comprising the capsid-like particles of claim 1.

17. The split-core carrier system as claimed in claim 6, wherein said pathogenic eukaryote is the malaria pathogen, *Plasmodium falciparum*.

18. The split-core carrier system as claimed in claim 1, wherein foreign molecule is a tumor marker protein.

19. The medicament as claimed in claim 14, wherein said foreign molecule comprises a surface protein of pathogenic Borreliae selected from the group consisting of OspA and OspC, and said medicament is a vaccine against lyme disease.

20. The medicament as claimed in claim 14, wherein said foreign molecule comprises the circumsporozoite protein from *Plasmodium falciparum* (CSP) or the C-terminally truncated version thereof (CSPshort) and said medicament is an immunogen against malaria.

21. The split-core carrier system of claim 1, wherein said system comprises two foreign molecules, wherein the first of the two is fused to the C-terminus of the core N-domain polypeptide and the second of the two is fused to the N-terminus of the core C-domain polypeptide.

22. The split-core carrier system of claim 21, wherein said two foreign molecules are peptides having different amino acid sequences.

* * * * *

UNITED STATES PATENT AND TRADEMARK OFFICE
CERTIFICATE OF CORRECTION

| | | |
|---|---|---|
| PATENT NO. | : 8,282,932 B2 | Page 1 of 1 |
| APPLICATION NO. | : 12/440454 | |
| DATED | : October 9, 2012 | |
| INVENTOR(S) | : Michael Nassal et al. | |

It is certified that error appears in the above-identified patent and that said Letters Patent is hereby corrected as shown below:

At column 35, line 33 (claim 2), replace the word "cure" with the word --core--.

Signed and Sealed this
Twenty-second Day of January, 2013

David J. Kappos
*Director of the United States Patent and Trademark Office*

SEQUENCE LISTING

```
<160> NUMBER OF SEQ ID NOS: 20

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly Thr Glu Asn Leu Tyr Phe Gln Gly Thr Gly Gly Gly
1               5                   10                  15

Gly

<210> SEQ ID NO 2
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Gly Gly Gly Ser Gly Gly Gly Val Glu Asp Gly Gly Gly Ser
1               5                   10                  15

Gly Gly Gly Gly Thr Ala Gln Leu Glu Lys Glu Leu Gln Ala Leu Glu
                20                  25                  30

Lys Glu Asn Ala Gln Leu Glu Trp Glu Leu Gln Ala Leu Glu Lys Glu
            35                  40                  45
```

```
Leu Ala Gln Thr Gly Glu Asn Leu Tyr Phe Gln Gly Thr Gly Gly Gly
    50                  55                  60

Gly
65
```

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggatccatga                                                          10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

```
His His His His His His
1               5
```

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      7xHis tag

<400> SEQUENCE: 5

```
His His His His His His His
1               5
```

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Gly Leu Asn Asp Ile Phe Glu Ala Gln Lys Ile Glu Trp His
1               5                   10
```

<210> SEQ ID NO 7
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gly Gly Gly Gly Ser Gly Gly Gly Val Glu Asp Gly Gly Gly Gly Ser
1               5                   10                  15

Gly Gly Gly Gly Thr Phe Asn Met Gln Gln Gln Arg Arg Phe Tyr Glu
            20                  25                  30

Ala Leu His Asp Pro Asn Leu Asn Glu Glu Gln Arg Asn Ala Lys Ile
```

```
                35                  40                  45

Lys Ser Ile Arg Glu Asp Pro
    50                  55

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Gly Gly Gly Ser Gly Gly Gly Gly Thr Gln Tyr Lys Leu Ile Leu
1               5                   10                  15

Asn Gly Lys Thr Leu Lys Gly Glu Thr Thr Thr Glu Ala Val Asp Ala
            20                  25                  30

Ala Thr Ala Glu Lys Val Phe Lys Gln Tyr Ala Asn Asp Asn Gly Val
        35                  40                  45

Asp Gly Glu Trp Thr Tyr Asp Asp Ala Thr Lys Thr Phe Thr Val Thr
    50                  55                  60

Glu Asp Pro
65

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Gly Gly Gly Thr Gln
1               5                   10

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaggatcctt ag                                                          12

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Ala Asn Pro
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 12

Asn Val Asp Pro
1

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ala Asn Pro Asn Val Asp Pro Asn Ala Asn Pro Asn Ala Asn Pro
1               5                   10                  15

Asn Ala Asn Pro Asn Val Asp Pro
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Glu Pro Ser Asp Lys His Ile Glu Gln Tyr Leu Lys Lys Ile Gln
1               5                   10                  15

Asn Ser Leu Ser
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Asn Gly Ile Gln Val Arg Ile Lys Pro Gly Ser Ala Asn Lys Pro
1               5                   10                  15

Lys Asp Glu Leu Asp
            20

<210> SEQ ID NO 16
<211> LENGTH: 183
<212> TYPE: PRT
<213> ORGANISM: Hepatitis B virus

<400> SEQUENCE: 16

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80
```

```
Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Glu
            20                  25                  30

Asp Pro

<210> SEQ ID NO 18
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Tyr Lys Leu Ile Leu Asn Gly Lys Thr Leu Lys Gly Glu Thr Thr Thr
1               5                   10                  15

Glu Ala Val Asp Ala Ala Thr Ala Glu Lys Val Phe Lys Gln Tyr Ala
            20                  25                  30

Asn Asp Asn Gly Val Asp Gly Glu Trp Thr Tyr Asp Asp Ala Thr Lys
        35                  40                  45

Thr Phe Thr Val Thr Glu
    50

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Gln Leu Glu Lys Glu Leu Gln Ala Leu Glu Lys Glu Asn Ala Gln
1               5                   10                  15

Leu Glu Trp Glu Leu Gln Ala Leu Glu Lys Glu Leu Ala Gln
            20                  25                  30
```

```
<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Gln Leu Lys Lys Lys Leu Gln Ala Leu Lys Lys Lys Asn Ala Gln
1               5                   10                  15

Leu Lys Trp Lys Leu Gln Ala Leu Lys Lys Lys Leu Ala Gln
            20                  25                  30
```